United States Patent
Ouyang

(10) Patent No.: US 12,059,036 B2
(45) Date of Patent: Aug. 13, 2024

(54) POWER SUPPLY COMPONENT OF ELECTRONIC ATOMIZATION DEVICE AND ELECTRONIC ATOMIZATION DEVICE

(71) Applicant: HONG KONG IVPS INTERNATIONAL LIMITED, Central (HK)

(72) Inventor: Junwei Ouyang, Shenzhen (CN)

(73) Assignee: HONG KONG IVPS INTERNATIONAL LIMITED, Central (HK)

( * ) Notice: Subject to any disclaimer, the term of this patent is extended or adjusted under 35 U.S.C. 154(b) by 721 days.

(21) Appl. No.: 17/356,634

(22) Filed: Jun. 24, 2021

(65) Prior Publication Data

US 2021/0401056 A1    Dec. 30, 2021

(30) Foreign Application Priority Data

Jun. 29, 2020   (CN) .......................... 202010602360.4

(51) Int. Cl.
*A24F 40/485*   (2020.01)
*A24F 40/51*    (2020.01)

(52) U.S. Cl.
CPC ............ *A24F 40/485* (2020.01); *A24F 40/51* (2020.01)

(58) Field of Classification Search
CPC ........ A24F 40/485; A24F 40/51; A24F 40/10; A24F 40/40; A24F 40/90; A61M 11/042; A61M 15/06
See application file for complete search history.

(56) References Cited

U.S. PATENT DOCUMENTS

2017/0295844 A1* 10/2017 Thevenaz ............. A24F 47/008

FOREIGN PATENT DOCUMENTS

CA          3066132 A1 *  4/2020   ........... A24B 15/167

* cited by examiner

*Primary Examiner* — Christopher M Rodd
*Assistant Examiner* — Daniel Edward Vakili
(74) *Attorney, Agent, or Firm* — Thompson Hine LLP

(57) ABSTRACT

The present is disclosure relates to a power supply component of an electronic atomization device. The power supply component includes an outer housing, a fixing holder, and an airflow trigger. The outer housing is provided with a collecting cavity. The fixing holder is installed on the bottom of collecting cavity. The bottom of the fixing holder is provided with an accommodating cavity. The airflow trigger locates at the open end of the accommodating cavity and forms a closed space with the accommodating cavity. The power supply component further includes an air column with one end closed. The open end of the air column communicates with the enclosed space. The side wall of the air column is provided with an air port in the collecting cavity to make the closed space and the collecting cavity connected.

18 Claims, 8 Drawing Sheets

POWER SUPPLY COMPONENT OF ELECTRONIC ATOMIZATION DEVICE AND ELECTRONIC ATOMIZATION DEVICE

CROSS-REFERENCE TO RELATED APPLICATION

This application claims priority to Chinese Patent Application No. 202010602360.4 filed on Jun. 29, 2020, which is incorporated herein by reference in its entirety.

TECHNICAL FIELD

This disclosure relates to the technical field of electronic atomization, especially a power supply component of electronic atomization device and an electronic atomization device.

BACKGROUND

An electronic atomization device is mainly composed of an atomization component and a power supply component. The power supply component is used for providing power to the atomization component. The atomization component heats and atomizes the liquid substrate to form inhalable aerosol for users. It is mainly used for quitting smoking. Since there is not harmful component, such as tar or suspended particulates that is usually contained in the traditional cigarettes, the electronic atomization device is gradually getting popular on the market.

When the power supply component provides power to the atomization component, it usually is controlled by a jog switch or a pneumatic switch in the traditional electronic atomization device. When the power supply component is controlled by the pneumatic switch, an air column is often provided with oppositely arranged air ports. When convection is occurred through these oppositely arranged air ports, the tobacco juice will enter the air column through one of these air ports, which will affect the trigger sensitivity of such pneumatic switch, and then impact on the normal function of such electronic atomization device.

SUMMARY

The main purpose of this disclosure is to provide a power supply component of electronic atomization device and an electronic atomization device, aiming to solve the current technical problem that the oil easily enters the pneumatic trigger switch of power supply component to cause trigger failure.

In order to achieve above-mentioned object, the present disclosure provides a power supply component of electronic atomization device. The power supply component of electronic atomization device includes an outer housing, a fixing holder, and an airflow trigger. The outer housing is provided with a collecting cavity. The top of the fixing holder is installed on the bottom of collecting cavity, and the bottom of the fixing holder locates outside of the collecting cavity. The bottom of the fixing holder is provided with an accommodating cavity. The airflow trigger is arranged at the open end of the accommodating cavity and forms a closed space with the accommodating cavity. The power supply component further includes an air column with one closed end. The air column is installed on the fixing holder, and the open end of the air column communicates with the enclosed space, wherein the side wall of the air column is provided with an air port in the collecting cavity to make the enclosed space and the collecting cavity connected.

In some implementations, there is a space between the air port and the bottom of the collecting cavity.

In some implementations, the opening of the air port faces toward the bottom of the collecting cavity in an oblique direction.

In some implementations, the diameter of the air port is about 0.8 mm-1.2 mm.

In some implementations, the power supply component further includes two conductive bouncing-pins. The air column locates at one side of the conductive bouncing-pins, so that the air column and the inlet channel on the atomization component of electronic atomization device are staggered-arranged.

In some implementations, the air ports are arranged on the side of the air column facing away from the conductive bouncing-pins.

In some implementations, the closed end of the air column is further provided with an end cap, and the diameter of the end cap is larger than the diameter of the air column.

In some implementations, the end cap is in a conical shape.

In some implementations, the outer surface of the fixing holder is covered with a silica gel layer. The silica gel layer is provided with a mounting hole for installing the air column, and the air column joints to the mounting hole in the manner of interference fit.

The present disclosure further provides an electronic atomization device. The electronic atomization device includes an atomization component and above-mentioned power supply component of electronic atomization device. The atomization component is installed in the collecting cavity of the power supply component.

The power supply component of electronic atomization device and the electronic atomization device are the technical solution of present disclosure. The power supply component includes an outer housing, a fixing holder, and an airflow trigger. The outer housing is provided with a collecting cavity. The fixing holder is installed on the bottom of collecting cavity. The outer housing is provided with a collecting cavity. The top of the fixing holder is installed on the bottom of collecting cavity, and the bottom of the fixing holder locates outside of the collecting cavity. The bottom of the fixing holder is provided with an accommodating cavity. The airflow trigger is arranged at the open end of the accommodating cavity and forms a closed space with the accommodating cavity. The power supply component further includes an air column with one closed end. The air column is installed on the fixing holder, and the open end of the air column communicates with the enclosed space, wherein the side wall of the air column is provided with an air port in the collecting cavity to make the enclosed space and the collecting cavity connected. With only one air port arranged on the air column, the air port locates in the collecting cavity and communicates with the airflow trigger. Under the function of this air port, it will be prevented that the oppositely arranged air ports induce tobacco juice to enter the air column due to air convection, resulting in the trigger failure. Simply providing one air port on the side wall of the air column, it can prevent tobacco juice from entering the air column and ensure that the airflow trigger normally controls power supply component to provide power to the atomization component, so that the electronic atomization device can work normally.

DESCRIPTION OF DRAWINGS

In order to more clearly explain the technical solutions in the embodiments of this disclosure or the prior art, drawings used in the description of the embodiments or the prior art are briefly introduced as below. Obviously, drawings in the following description are only used for some embodiments of this disclosure. For those of ordinary skill in the art, other drawings can be obtained according to the structure shown in these drawings without any other creative effort.

DESCRIPTION OF DRAWING LABELS

Figure 1:
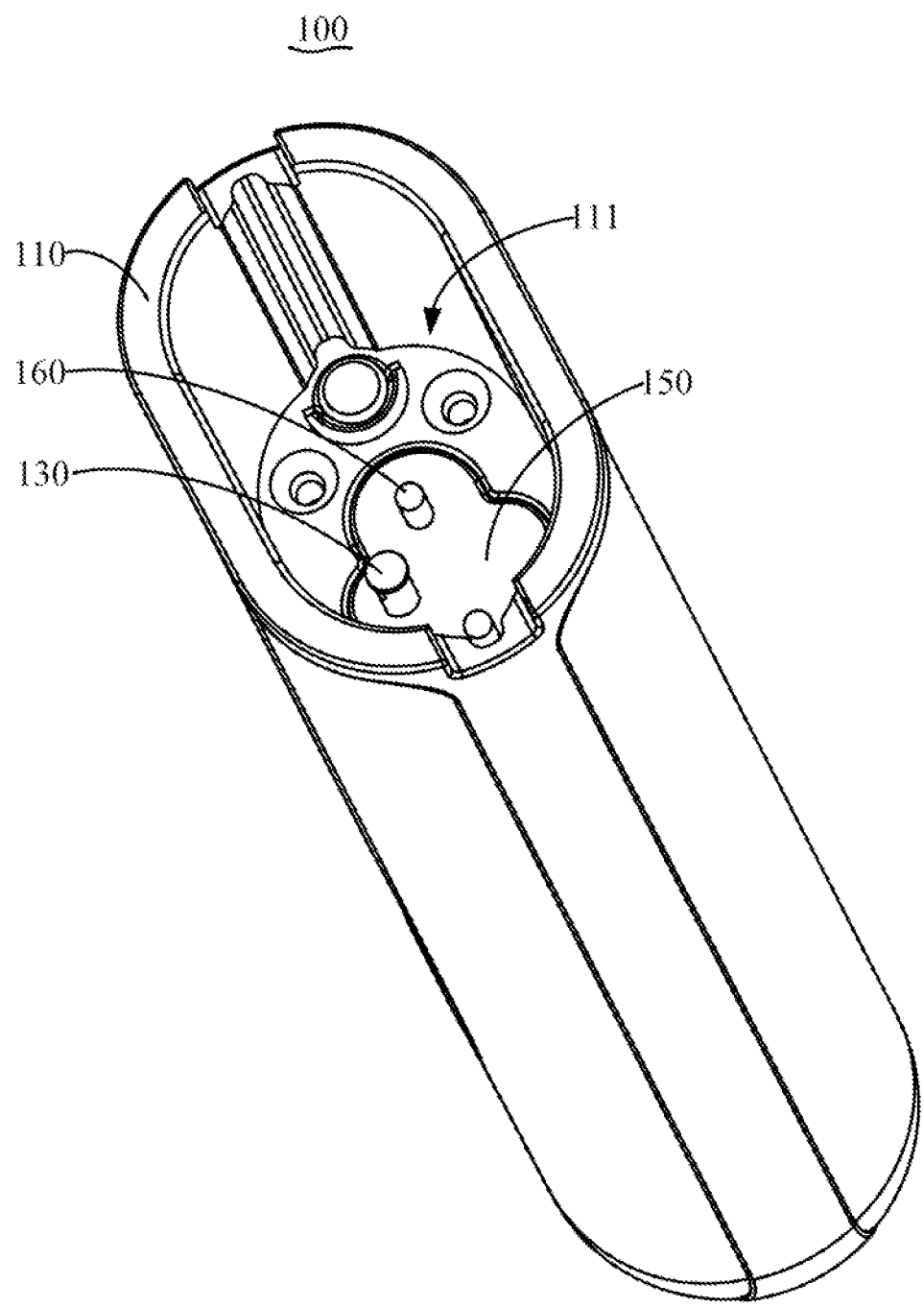
FIG. 1 is the three-dimensional schematic diagram of the power supply component of electronic atomization device in this disclosure.
Figure 2:
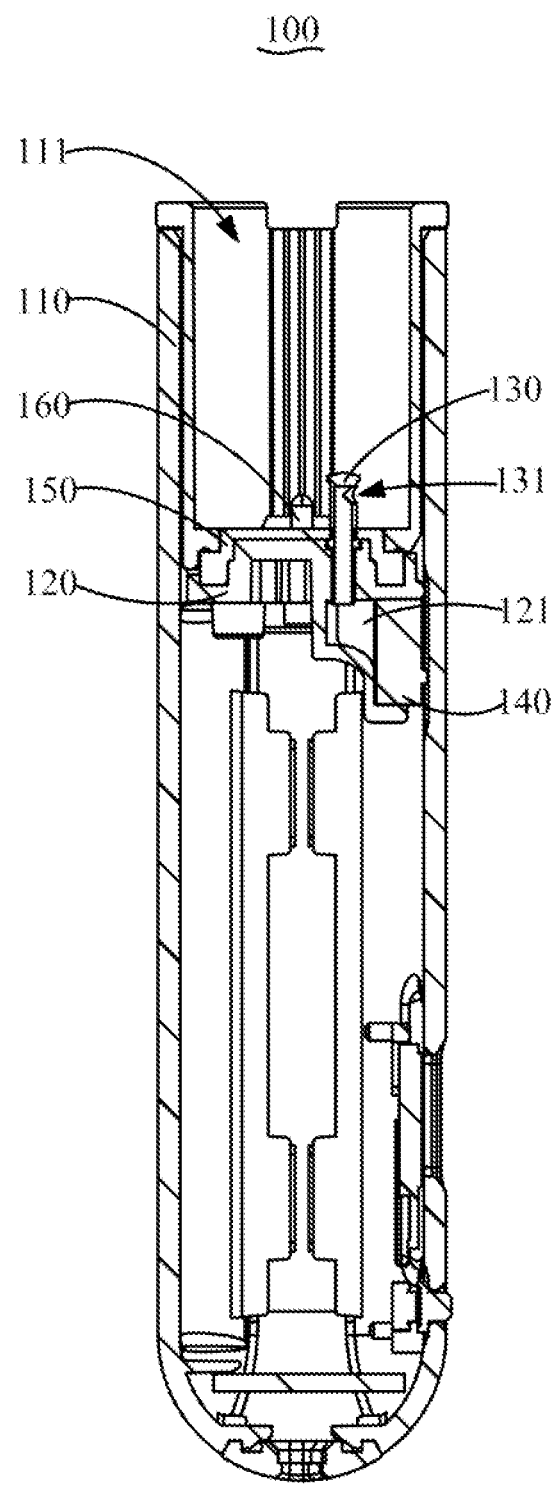
FIG. 2 is the cross-sectional schematic diagram of power supply component shown in FIG. 1.

| Label | Name | Label | Name |
| --- | --- | --- | --- |
| 100 | Power supply component | 110 | Outer housing |
| 111 | Collecting cavity | 120 | Fixing holder |
| 121 | Closed space | 130 | Air column |
| 131 | Air port | 132 | End cap |
| 140 | Airflow trigger | 150 | Silica gel layer |
| 160 | Conductive bouncing-pin | 200 | Atomization component |
| 1000 | Electronic atomization device | 122 | Accommodating cavity |

The purpose, functional characteristics, and advantages of present disclosure will be further explained with the reference to embodiments and drawings.

DETAILED DESCRIPTION OF THE INVENTION

The technical solutions in the embodiments of present disclosure will be clearly and completely described as below with reference to drawings in the embodiments of present disclosure. Obviously, any described embodiment is only a part of embodiments of this present disclosure, but not all of them. Based on the embodiments of present disclosure, any other embodiment obtained by a person of ordinary skill in the art without any creative efforts shall be within the protection scope of this present disclosure.

It should be noted that any directional indication (such as up, down, left, right, front, and back . . . ) in the embodiment of present disclosure is only used to explain the relative positional relationship and movement of elements in a specific posture (as shown in drawings). If such specific posture changes, the directional indication will change accordingly.

In addition, the descriptions related to "first", "second", etc. in the present disclosure are for descriptive purposes only and cannot be understood as any indication or implication of its relative importance or implicit indication of the number of technical features. Therefore, any feature defined as "first" or "second" may explicitly or implicitly include at least one of features. In addition, any technical solutions in various embodiments can be combined with each other but must be realized by a person of ordinary skill in the art. When such combination of technical solutions shows conflicts or cannot be achieved, it should be considered as nonexistent and will not be within the protection scope claimed by this present disclosure.

In the present disclosure, the terms of "connected" and "fixed" shall be understood in a broad sense unless otherwise specified and defined; for example, "fixed" may be a fixed connection, a detachable connection, or an integral one; It can be a mechanical connection or an electrical connection; it also can be directly connected or indirectly connected through an intermediate medium; it also can be an internal connection of two elements or an interaction relationship between two elements, unless specifically defined otherwise. For those of ordinary skill in the art, they can explain specific meanings of above terms in the present disclosure according to the specific situation.

The present disclosure provides an electronic atomization device. The electronic atomization device includes a power supply component and an electric connection of this power supply component. The power supply component is provided with a rechargeable power supply and a main control board electrically connected to the power supply. The atomization component is fixed on or detachedly installed on the power supply component. The atomization component is provided with an inhalation channel and a collecting space. The collecting space is filled with tobacco juice or tobacco paste, and the inhalation channel is further provided with an atomization core in the collecting space. The main control board provided in the power supply component controls the output current of power supply to provide power to the atomization component, so that the atomization core of atomization component can heat the tobacco juice under driving from power supply component, and users can inhale it to obtain smoking experience. At the same time, there is a plug-in terminal component for charging and data transmission. The plug-in terminal component can be a micro-type charging socket, lightning-type charging socket, or type-c charging socket, etc.

Reference to FIG. 1 to FIG. 9, the present disclosure provides a power supply component 100 of electronic atomization device 1000. The power supply component 100 includes an outer housing 110, a fixing holder 120, and an airflow trigger 140. The outer housing 110 is provided with a collecting cavity 111. The top of the fixing holder 120 is installed on the bottom of collecting cavity 111, and the bottom of the fixing holder 120 locates outside of the collecting cavity 111. The bottom of the fixing holder 120 is provided with an accommodating cavity 122. The airflow trigger 140 is arranged at the open end of the accommodating cavity 122 and forms a closed space 121 with the accommodating cavity 122. The power supply component 100 further includes an air column 130 with one closed end. The air column 130 is installed on the fixing holder 120, and the open end of the air column 130 communicates with the enclosed space 121, wherein the side wall of the air column 130 is provided with an air port 131 in the collecting cavity 111 to make the closed space 121 and the collecting cavity 111 connected.

Specifically, the electronic atomization device 1000 includes a power supply component 100 and an atomization component 200. The outer housing 110 is provided with a collecting cavity 111. When the atomization component 200 works with the power supply component 100, the atomization component 200 will be installed inside the collecting cavity 111. The bottom of the collecting cavity 111 is provided with a hole. The fixing holder 120 is installed on the bottom of the collecting cavity 111, and the fixing holder 120 is aligned with the back side of bottom of the collecting cavity 111. The fixing holder 120 connects to the outer housing 110 in a manner of screw fasten; in addition, the top of the fixing holder 120 is aligned with the bottom surface of the collecting cavity 111 to enhance the integrity of the collecting cavity 111. The bottom of the fixing cavity 122 and the collecting cavity 111 locate on opposite sides of top end of the fixing cavity 122. The fixing cavity 122 is provided with an accommodating cavity 122 on the side away from the collecting cavity 111. The open end of the accommodating cavity 122 away from the collecting cavity 111 is set on the fixing holder 120. The airflow trigger 140 is arranged on the open end of the accommodating cavity 122. The airflow trigger 140 can be an airflow sensor. The edge of the airflow trigger 140 adheres with the inner side wall of the accommodating cavity 122, so that the airflow trigger 140 can fasten-connects to the fixing holder 120. In addition, the airflow trigger 140 and the bottom of the accommodating cavity 122 enclose to form a closed space 121. The inductive surface of the airflow trigger 140 faces to the closed space 121. The airflow trigger 140 is next to the patch of power supply component 100, so that the air can enter the detection air channel of the airflow trigger 140 through the gap.

The power supply component 100 may further include an air column 130. The air column 130 is hollow. The air column 130 has two opposite ends; wherein, one end of the air column 130 is closed, and the other end of the air column 130 communicates with outside. The air column 130 is installed on the fixing holder 120, and the air column 130 is perpendicular to the fixing holder 120. The closed end of the air column 130 is exposed in the collecting cavity 111. The open end of the air column 130 communicates with the closed space 121. Under the structural function of the air column 130, the inductive surface of the airflow trigger 140 will detect any air flowing in the collecting cavity 111 to determine whether user is doing suction. The side wall of the air column 130 is provided with only one air port 131. The air port 131 locates inside the collecting cavity 111; that is, the air port 131 is next to the closed end of the air column 130.

In above technical solution, the side wall of the air column 130 is only provided with one air port 131, and the air port 131 locates inside the collecting cavity 111. Because there is only one air port 131 on the side wall of the air column, the air can only flow from the closed space 121 into the collecting cavity 111 through the air port 131, so as to prevent tobacco juice from entering the air column 130 through the air port 131. When there are two or more air ports on the side wall of the air column 130, convection will occur due to the short distance between one and the other port, resulting in air flowing-in through some air ports; such phenomenon will drive tobacco juice on the outer surface of the air column to flow into the air column 130. In this embodiment, the air column 130 is provided with only one the air port 131, in order to prevent tobacco juice leaked on the atomization component 200 from entering the air column 130 along the outer wall of the air column 130; in addition, it can ensure that the airflow trigger 140 will be triggered sensitively in order to keep the atomization power supply component 100 work normally.

In an optional embodiment, a space is provided between the air port 131 and the bottom of the collecting cavity 111. It is understandable that the air port 131 can also be adjacent to the bottom of the collecting cavity 111. In this embodiment, there is a space between the air port 131 and the collecting cavity 111; that is, the air port 131 is apart from the bottom of the collecting cavity 111 in order to prevent tobacco juice leaked on the bottom of the collecting cavity 111 from entering the air port 131 along the bottom of the collecting cavity 111, which will keep the closed space 121 clean, avoid any impact on the detection sensitivity of the airflow trigger 140, and ensure normal power supply to the atomization component 200 provided by the power supply component 100.

Figure 6:
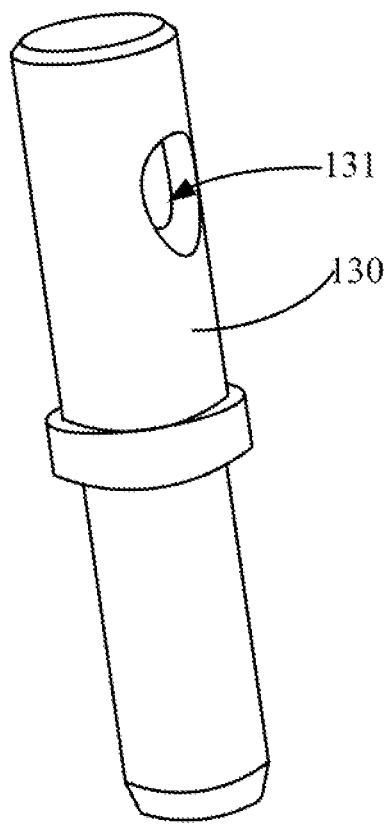
FIG. 6 is another embodiment's three-dimensional schematic diagram of air column of power supply component in this disclosure.
Figure 7:
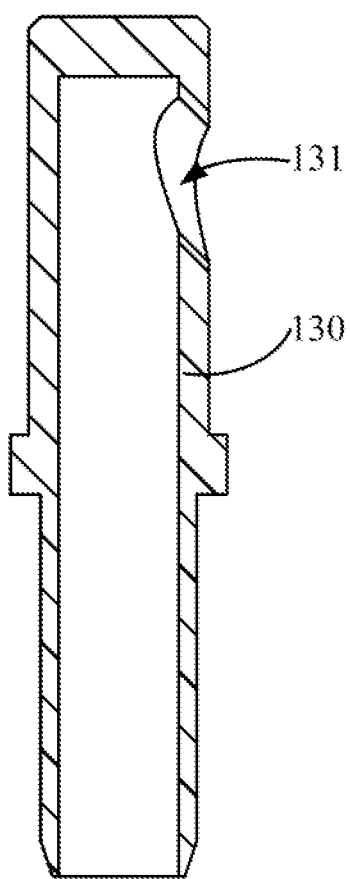
FIG. 7 is the cross-sectional schematic diagram of air column shown in FIG. 6.

Reference to FIG. 6 and FIG. 7, the structural diagram of another embodiment of air column 130, in an optional embodiment, the opening of the air port 131 faces toward the bottom of the collecting cavity 111 in an oblique direction. In this embodiment, the air column 130 is perpendicular to the collecting cavity 111. The angle between the axis of the air port 131 and the axis of the air column 130 is less than 90°; for example, the angle between the axis of the air port 130 and the axis of the air column 130 can be 30°, 45°, or 60°; the air port 131 is tilted down. When there is tobacco juice on the outer surface of the air column 130, because the opening direction of the air port 131 is tilted, the tobacco juice on the cylindrical surface of the air column 130 will drop down directly from the edge of the air port 131 under the gravity, and the leaked tobacco juice will not enter the air column 130 along the side wall of the air port 131, so as to keep the air column 130 clean and ensure any air flowing can be detected normally by the airflow trigger 140.

In an optional embodiment, the diameter of the air port 131 is about 0.8 mm-1.2 mm. When the diameter of the air port 131 is within 0.8 mm-1.2 mm, the air in the collecting cavity 111 can easily drive the air inside the air column to flow, thereby facilitating the airflow trigger 140 to detect any suction performed by the user. It is understandable that the diameter of the air port 131 can be 0.8 mm, 0.9 mm, 1 mm, 1.1 mm, or 1.2 mm. In this embodiment, the diameter of the air port 131 is 1 mm, and it is easy to design and process the air port 131. In addition, it is also easy for the airflow trigger 140 to detect whether the atomization component 200 of electronic atomization device 1000 is sucked by the user.

Figure 3:
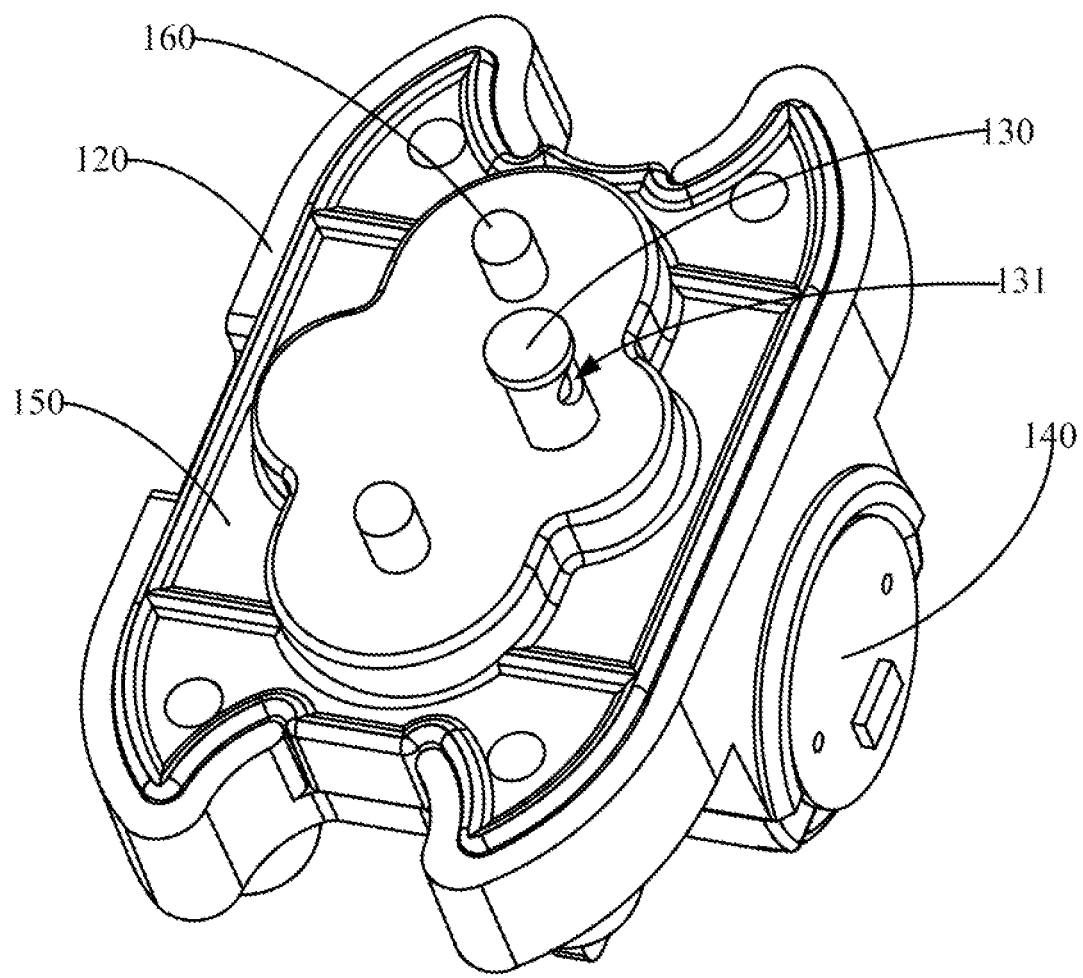
FIG. 3 is the three-dimensional schematic diagram of fixing holder and air column of power supply component shown in FIG. 1.
Figure 4:
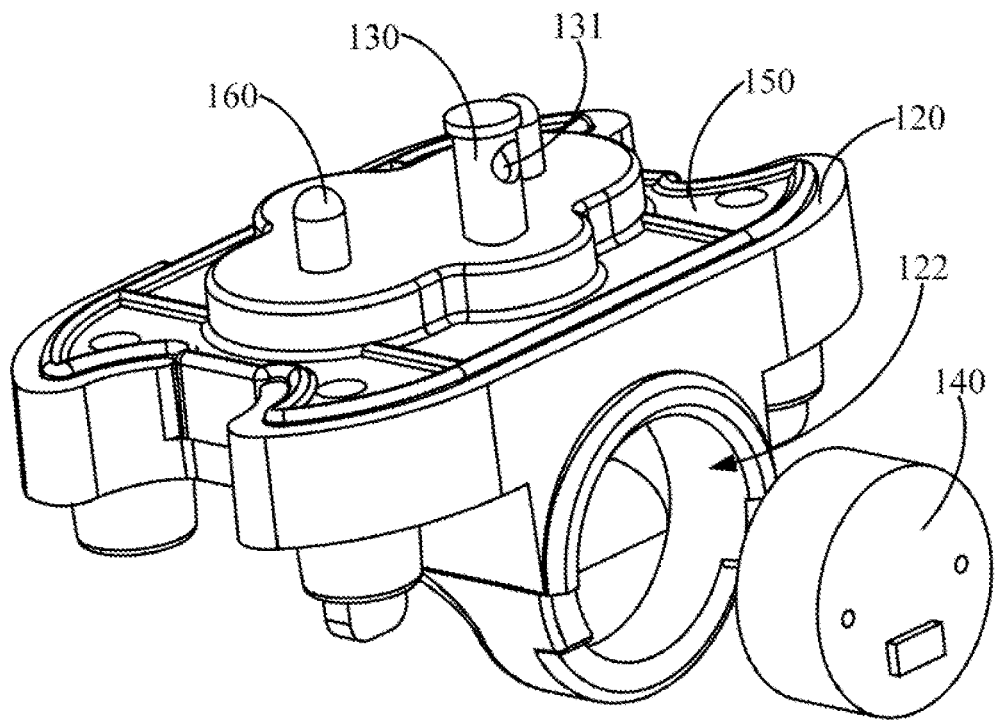
FIG. 4 is the explosion schematic diagram of fixing holder and air column of power supply component shown in FIG. 1.
Figure 5:
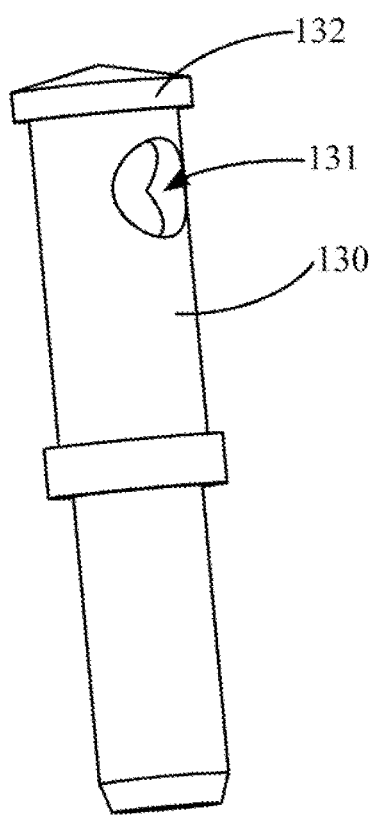
FIG. 5 is the three-dimensional schematic diagram of air column of power supply component shown in FIG. 1.

Please keep the reference to FIG. 3 to FIG. 5. In an optional embodiment, the outer surface of the fixing holder 120 is covered with a silica gel layer 150. The silica gel layer 150 is provided with an installation hole for installing the air column 130. The air column 130 joins with the installation hole in the manner of interference fit. The silica gel layer 150 covers the fixing holder 120 and one side of bottom of the collecting cavity. The silica gel layer 150 connects to the fixing holder in the manner of adhesion, integral molding, or buckle connection. When the fixing holder 120 is installed on the outer housing, the silica gel layer 150 is aligned with the bottom of the collecting cavity 111, wherein the silica gel layer 150 covers the hole on the bottom of the collecting cavity 111. In addition, when the fixing holder 120 is installed on the outer housing 110, the edge of the silica gel layer 150 locates at the space between the bottom of the collecting cavity 111 and the fixing holder 120. The edge of the silica gel layer 150 is provided with a boss. When the fixing holder 120 is installed on the bottom of the collecting cavity 111, the silica gel layer 150 tightly abuts the bottom of the collecting cavity 111 in order to prevent leaked tobacco juice from leaking the power supply component 100 through the joint of the silica gel layer 150 and the collecting cavity 111. In this embodiment, the silica gel layer 150 is provided with an installation hole. The air column 130 joins with the installation hole in the manner of interference fit, in order to prevent tobacco juice from leaking the closed space 121 through the edge of the air column 130, ensure no tobacco juice can enter into the closed space 121, and keep the power supply component 100 working normally.

Please keep reference to FIG. 1 to FIG. 5. In an optional embodiment, the power supply component 100 further includes two conductive bouncing-pins 160. The air column 130 locates at one side of the conductive bouncing-pins 160, so that the air column 130 and the inlet channel on the atomization component 200 of electronic atomization device 1000 are stagger-arranged. Two the conductive bouncing-pins 160 are the positive and negative electrodes of the power supply component 100; wherein two the conductive bouncing-pins 160 are installed on the fixing holder 120, and the conductive bouncing-pins 160 tightly fit with the installation position on the silica gel layer 150 in order to prevent tobacco juice from leaking through the gap on the installation position of the conductive bouncing-pins 160. When the atomization component 200 is installed in the collecting cavity 111 of outer housing 110, the inlet channel of atomization component 200 usually locates at the central position of the collecting cavity 111. In this embodiment, the two conductive bouncing-pins 160 are on the symmetry planes of the collecting cavity 111. The inlet channel of the atomization component 200 locates at the central position of the two conductive bouncing-pins. The air column 130 is next to the edge of the fixing holder 120. The air column 130 and the two conductive bouncing-pins 160 are non-collinear; that is, the air column 130 is on one side of connecting line between the two conductive bouncing-pins 160, and the air column 130 deviates from the connecting line between the two conductive bouncing-pins 160, so the air column 130 and the inlet channel of atomization component 200 are not on the same vertical line. Therefore, when the atomization core of atomization component 200 is leaking, leaked tobacco juice will drip down along the inlet channel but not drop on the air column 130, which will reduce the amount of tobacco juice remaining on the air column 130, and then further reduce the possibility that tobacco juice enters the air column 130.

The fixing holder 120 may be installed behind the silica gel layer 150. When the conductive bouncing-pin 160 and the air column 130 are installed on the fixing holder 120, the fixing holder 120, the conductive bouncing-pin 160, and the air column 130 will be assembled and joints with the bottom of the air column 130, which will be easier for installing the conductive bouncing-pin 160 and the air column 130 inside the collecting cavity 111.

In an optional embodiment, the air ports 131 are arranged on the side of the air column 130 facing away from the conductive bouncing-pins 160. In this embodiment, the air column 130 is only provided with one air port 131. The air port 131 is away from the inlet channel of the atomization component 200, so that the air port 131 can be away from the inlet channel as far as possible in order to prevent any leaked tobacco juice in the atomization corn from entering the closed space 121 through the air port 131.

Please keep reference to FIG. 2 to FIG. 5. In an optional embodiment, the closed end of the air column 130 is further provided with an end cap 132, and the diameter of the end cap 132 is larger than that of the air column 130. The end cap 132 is set on the top of the air column 130; that is, the end cap 132 is set at the closed end of the air column 130, and any tobacco juice leaked from the atomization component 200 will drop down on the end cap 132. In this embodiment, the end cap 132 and the air column 130 are integrative, and the structure is quite simple. When any tobacco juice drops on the end cap 132, the tobacco juice will drop down from the edge of the end cap 132. Because the outer diameter of the end cap 132 is larger than that of the air column 130, the tobacco juice on the end cap 132 will not slide down along the side wall of the air column 130, which will prevent the tobacco juice from entering the air port 131 and ensure the clean inside the closed space 121.

In an optional embodiment, the end cap 132 is in a conical shape. In this embodiment, when any tobacco juice drips down on the end cap 132, the tobacco juice will slide down to the edge along the side wall of the end cap 132 and then drips down, so as to facilitate the tobacco juice to leave from the air column 130. In addition, the angle between the side plane of the end cap 132 and the horizontal plane is around 10° to 15°, which will reduce the height of the air column 130 and be easier for the tobacco juice to leave from the closed end of the air column 130.

The bottom of the collecting cavity 111 may include two magnets. The two magnets are symmetrically arranged in the collecting cavity 111. Under the action of these magnets, when the atomization component 200 is installed inside the collecting cavity of outer housing 110, it will be easier for the atomization component 200 to joint with the power supply component 100 and prevent the atomization component 200 from shaking inside the collecting cavity 111.

Figure 8:
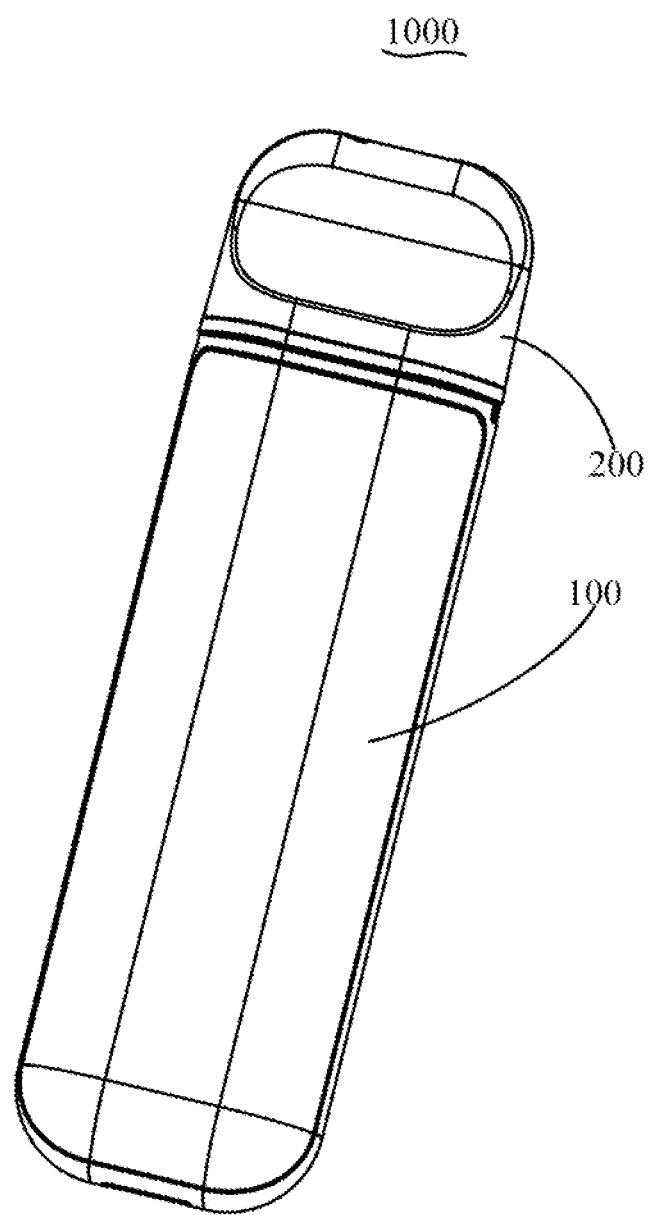
FIG. 8 is the three-dimensional schematic diagram of electronic atomization device in this disclosure.
Figure 9:
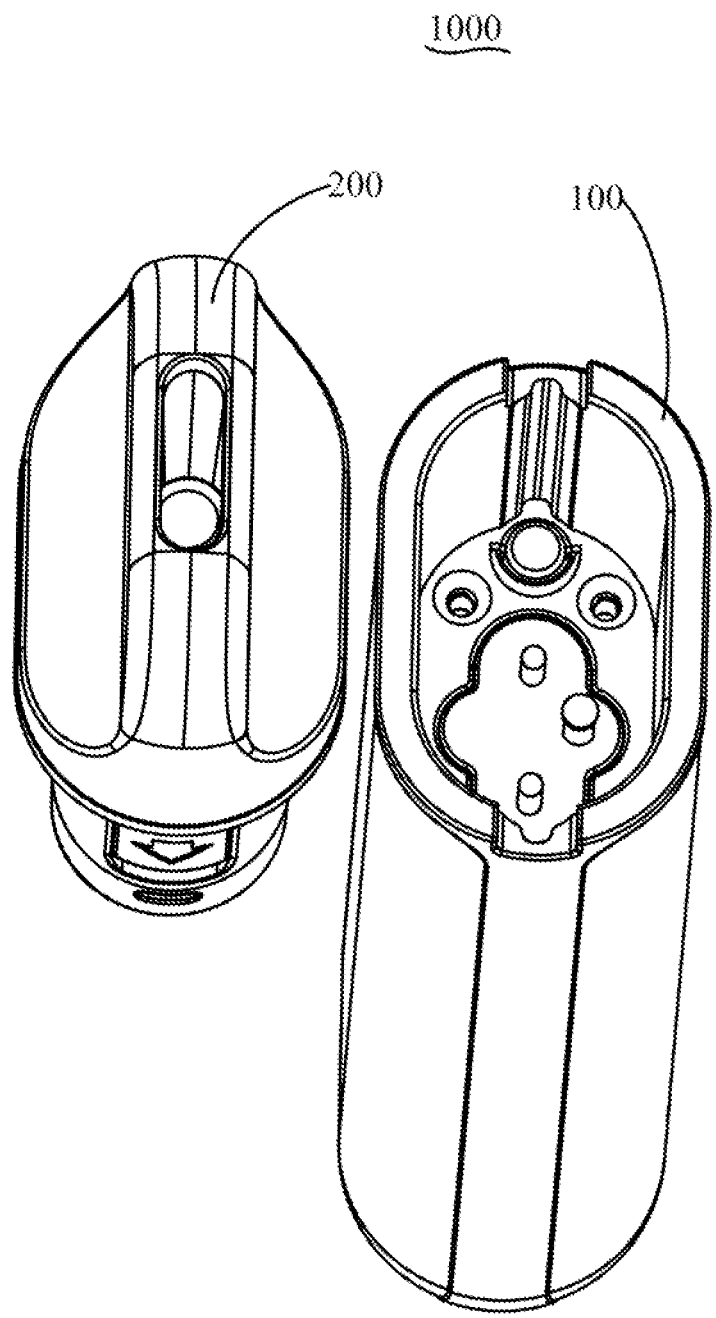
FIG. 9 is the explosion schematic diagram of electronic atomization device shown in FIG. 8.

In reference to FIG. 8 and FIG. 9, the present disclosure also provides an electronic atomization device 1000. The electronic atomization device 1000 includes an atomization component 200 and a power supply component 100 of above-mentioned electronic atomization device 1000. The atomization component 200 is installed inside the collecting cavity 111 of the power supply component 100, and the power supply component 100 electronically connects to the atomization component 200. The specific structure of power supply component 100 of electronic atomization device 1000 can be referred to the foregoing embodiments. Since the electronic atomization device 1000 adopts all technical solutions described in the foregoing embodiments, it has at least all benefits brought by technical solutions of foregoing embodiments. The effects will not be repeated here.

The above is only the preferred embodiment of present disclosure, but not limit the patent scope of present disclosure. Any equivalent structural transformation that is under the inventive concept of present disclosure and made by using description and drawings of present disclosure, or directly/indirectly use such transformation in any other related technical fields are all covered by the patent protection scope of present disclosure.

The invention claimed is:

1. A power supply component of an electronic atomization device, the power supply component comprising:
    an outer housing including a collecting cavity;
    a fixing holder, wherein a top of the fixing holder is installed on a bottom of the collecting cavity, a bottom of the fixing holder is located outside of the collecting cavity, and the bottom of the fixing holder includes an accommodating cavity;
    an airflow trigger located at an open end of the accommodating cavity and forms a closed space with the accommodating cavity; and
    an air column comprising a closed end that is installed on the fixing holder and an open end that communicates with the closed space, wherein the side wall of the air column includes an air port in the collecting cavity that is configured to connect the closed space and the collecting cavity.

2. The power supply component of claim 1, wherein there is a space between the air port and the bottom of the collecting cavity.

3. The power supply component of claim 2, wherein an opening of the air port faces toward the bottom of the collecting cavity in an oblique direction.

4. The power supply component of claim 1, wherein the diameter of the air port ranges between 0.8 mm-1.2 mm.

5. The power supply component of claim 1, further including two conductive bouncing-pins, wherein an air column is located at one side of the conductive bouncing-pins, such that the air column and inlet channels on the atomization component of the electronic atomization device are stagger-arranged.

6. The power supply component of claim 5, wherein the air port is arranged on a side of the air column facing away from the conductive bouncing-pins.

7. The power supply component of claim 1, wherein the closed end of the air column is further provided with an end cap, and the diameter of the end cap is larger than a diameter of the air column.

8. The power supply component of claim 1, wherein the end cap comprises a conical shape.

9. The power supply component of claim 1, wherein the outer surface of the fixing holder comprises a silica gel layer that includes a mounting hole for installing the air column, and the air column is configured to connect with the mounting hole based on interference fit.

10. An electronic atomization device, comprising:
an atomization component; and
a power supply component comprising:
an outer housing including a collecting cavity, wherein the atomization component is installed inside the collecting cavity;
a fixing holder, wherein a top of the fixing holder is installed on a bottom of the collecting cavity, a bottom of the fixing holder is located outside of the collecting cavity, and the bottom of the fixing holder includes an accommodating cavity;
an airflow trigger located at an open end of the accommodating cavity and forms a closed space with the accommodating cavity; and
an air column comprising a closed end that is installed on the fixing holder and an open end that communicates with the closed space, wherein the side wall of the air column includes an air port in the collecting cavity that is configured to connect the closed space and the collecting cavity.

11. The electronic atomization device of claim 10, wherein there is a space between the air port and the bottom of the collecting cavity.

12. The electronic atomization device of claim 11, wherein an opening of the air port faces toward the bottom of the collecting cavity in an oblique direction.

13. The electronic atomization device of claim 10, wherein the diameter of the air port ranges between 0.8 mm-1.2 mm.

14. The electronic atomization device of claim 10, wherein the power supply component further includes two conductive bouncing-pins, wherein an air column is located at one side of the conductive bouncing-pins, such that the air column and inlet channels on the atomization component of the electronic atomization device are stagger-arranged.

15. The electronic atomization device of claim 14, wherein the air port is arranged on a side of the air column facing away from the conductive bouncing-pins.

16. The electronic atomization device of claim 10, wherein the closed end of the air column is further provided with an end cap, and the diameter of the end cap is larger than a diameter of the air column.

17. The electronic atomization device of claim 10, wherein the end cap comprises a conical shape.

18. The electronic atomization device of claim 10, wherein the outer surface of the fixing holder comprises a silica gel layer that includes a mounting hole for installing the air column, and the air column is configured to connect with the mounting hole based on interference fit.

* * * * *